US012270185B2

United States Patent
Thomsson et al.

(10) Patent No.: US 12,270,185 B2
(45) Date of Patent: Apr. 8, 2025

(54) COMPOSITIONAL MULTISPECTRAL AND HYPERSPECTRAL IMAGING SYSTEMS FOR MINING SHOVELS AND ASSOCIATED METHODS

(71) Applicant: MineSense Technologies Ltd., Vancouver (CA)

(72) Inventors: Daniel Thomsson, Burnaby (CA); Maarten Heast, Vancouver (CA)

(73) Assignee: MineSense Technologies Ltd., Vancouver (CA)

( * ) Notice: Subject to any disclaimer, the term of this patent is extended or adjusted under 35 U.S.C. 154(b) by 22 days.

(21) Appl. No.: 17/992,626

(22) Filed: Nov. 22, 2022

(65) Prior Publication Data

US 2023/0160182 A1    May 25, 2023

Related U.S. Application Data

(60) Provisional application No. 63/282,087, filed on Nov. 22, 2021.

(51) Int. Cl.
*H04N 23/10* (2023.01)
*B60R 11/04* (2006.01)
(Continued)

(52) U.S. Cl.
CPC .............. *E02F 9/261* (2013.01); *B60R 11/04* (2013.01); *G01N 21/27* (2013.01); *H04N 23/10* (2023.01);
(Continued)

(58) Field of Classification Search
None
See application file for complete search history.

(56) References Cited

U.S. PATENT DOCUMENTS

| 719,343 A | 1/1903 | Langerfeld |
| 3,049,308 A | 8/1962 | Lang |

(Continued)

FOREIGN PATENT DOCUMENTS

| AU | 2006249259 | 6/2007 |
| CA | 2629408 | 11/2009 |

(Continued)

OTHER PUBLICATIONS

Examination Report for Australian Patent Application No. 2023202061, mailed Jul. 28, 2023, 4 pages.
(Continued)

*Primary Examiner* — Cynthia Segura
(74) *Attorney, Agent, or Firm* — Taft Stettinius & Hollister LlP (57) ABSTRACT

Mining shovel with compositional multispectral and/or hyperspectral imaging and associated methods and systems are disclosed herein. In some embodiments, a mining detection system includes a mining bucket carrying a multispectral and/or hyperspectral imaging system and various sensors directed toward material entering and positioned within the bucket. The bucket can also carry a control enclosure housing image and sensor processing equipment that receives and analyzes the data collected by the multispectral and/or hyperspectral imaging system and the sensors. The disclosed systems and methods can provide real-time compositional analysis of mined materials at the mining site, which can be used to manage a mining field, including generating and transmitting instructions for where the material within the bucket should be delivered based on the data collected from the multispectral and/or hyperspectral imaging system and the sensors.

27 Claims, 7 Drawing Sheets

(51) Int. Cl.

| | | |
|---|---|---|
| *E02F 9/26* | (2006.01) | |
| *G01N 21/27* | (2006.01) | |
| *H04N 23/56* | (2023.01) | |
| *H04N 23/57* | (2023.01) | |
| *B60R 11/00* | (2006.01) | |
| *G01N 21/17* | (2006.01) | |
| *G01N 33/24* | (2006.01) | |

(52) U.S. Cl.
CPC ............ *H04N 23/56* (2023.01); *H04N 23/57* (2023.01); *B60R 2011/004* (2013.01); *G01N 2021/1776* (2013.01); *G01N 33/24* (2013.01)

(56) References Cited

U.S. PATENT DOCUMENTS

| | | | |
|---|---|---|---|
| 3,209,910 | A | 10/1965 | Palmer |
| 3,263,160 | A | 7/1966 | Dolan et al. |
| 3,337,328 | A | 8/1967 | Lawver |
| 3,655,964 | A | 4/1972 | Slight |
| 3,701,419 | A | 10/1972 | Hutter |
| 3,747,755 | A | 7/1973 | Senturia et al. |
| 4,006,481 | A | 2/1977 | Young et al. |
| 4,030,026 | A | 6/1977 | Payne |
| 4,128,803 | A | 12/1978 | Payne |
| 4,236,640 | A | 12/1980 | Knight |
| 4,241,835 | A | 12/1980 | Lockett |
| 4,300,097 | A | 11/1981 | Turner |
| 4,361,238 | A | 11/1982 | Kealy et al. |
| 4,365,719 | A | 12/1982 | Kelly |
| 4,441,616 | A | 4/1984 | Konig et al. |
| 4,507,612 | A | 3/1985 | Payne |
| 4,600,356 | A | 7/1986 | Bridges et al. |
| 4,659,989 | A | 4/1987 | Kerr |
| 4,909,930 | A | 3/1990 | Cole |
| 5,197,607 | A | 3/1993 | Hakansson |
| 5,236,092 | A | 8/1993 | Krotkov |
| 5,285,972 | A | 2/1994 | Notebaart |
| 5,413,222 | A | 5/1995 | Holder |
| 5,523,690 | A | 6/1996 | Rowan |
| 5,592,092 | A | 1/1997 | Mechler |
| 5,813,543 | A | 9/1998 | Gesing et al. |
| RE36,537 | E | 2/2000 | Sommer et al. |
| 6,078,018 | A | 6/2000 | Davis et al. |
| 6,140,643 | A | 10/2000 | Brown |
| 6,444,936 | B1 | 9/2002 | Ludwig et al. |
| 6,545,240 | B2 | 4/2003 | Kumar |
| 6,664,914 | B2 | 12/2003 | Longstaff et al. |
| 6,693,274 | B2 | 2/2004 | Baird |
| 6,753,957 | B1 | 6/2004 | Graft et al. |
| 6,817,474 | B2 | 11/2004 | Ikeda |
| 7,161,672 | B2 | 1/2007 | Gronushkin et al. |
| 7,430,273 | B2 | 9/2008 | Yellepeddi |
| 7,564,943 | B2 | 7/2009 | Sommer et al. |
| 7,574,821 | B2 | 8/2009 | Furem |
| 7,595,489 | B2 | 9/2009 | Statham |
| 7,737,379 | B2 | 6/2010 | Witdouck |
| 7,763,820 | B1 | 7/2010 | Sommer et al. |
| 7,786,401 | B2 | 8/2010 | Valerio |
| 7,797,861 | B2 | 9/2010 | Wright |
| 7,909,169 | B1 | 3/2011 | Slade |
| 7,948,237 | B2 | 5/2011 | Kuzmin et al. |
| 7,965,167 | B2 | 6/2011 | Volker et al. |
| 7,970,574 | B2 | 6/2011 | Jin |
| 8,100,581 | B2 | 1/2012 | Djordjevic |
| 8,138,437 | B2 | 3/2012 | Valerio |
| 8,315,838 | B2 | 11/2012 | Durrant-Whyte |
| 8,446,156 | B2 | 5/2013 | Morrison |
| 8,476,545 | B2 | 7/2013 | Sommer |
| 8,494,220 | B2 | 7/2013 | Del Grande |
| 8,515,008 | B2 | 8/2013 | Ulberg et al. |
| 8,600,545 | B2 | 12/2013 | Earlam |
| 8,664,595 | B2 | 3/2014 | Buhot et al. |
| 8,766,129 | B2 | 7/2014 | Kazakov et al. |
| 8,812,149 | B2 | 8/2014 | Doak |
| 8,820,533 | B2 | 9/2014 | Shaw et al. |
| 8,841,571 | B2 | 9/2014 | Tavakkoli |
| 8,843,266 | B2 | 9/2014 | Lindskov |
| 8,855,809 | B2 | 10/2014 | Spencer et al. |
| 8,875,901 | B2 | 11/2014 | Wellwood et al. |
| 8,908,829 | B2 | 12/2014 | Watanabe et al. |
| 8,931,720 | B2 | 1/2015 | Box et al. |
| 8,937,282 | B2 | 1/2015 | Owen et al. |
| 8,957,340 | B2 | 2/2015 | Wellwood et al. |
| 8,958,905 | B2 | 2/2015 | Bamber et al. |
| 9,010,543 | B2 | 4/2015 | Box et al. |
| 9,114,433 | B2 | 8/2015 | Roos et al. |
| 9,237,284 | B2 | 1/2016 | Hogasten |
| 9,278,670 | B2 | 3/2016 | Hattori et al. |
| 9,290,913 | B2 | 3/2016 | Bamber et al. |
| 9,314,823 | B2 | 4/2016 | Bamber et al. |
| 9,316,537 | B2 | 4/2016 | Bamber et al. |
| 9,604,826 | B2 | 3/2017 | Fretz |
| 9,764,361 | B2 | 9/2017 | Valerio |
| 9,785,851 | B1 | 10/2017 | Torek |
| 9,884,346 | B2 | 2/2018 | Bamber et al. |
| 9,958,407 | B2 | 5/2018 | Bamber et al. |
| 10,029,284 | B2 | 7/2018 | Bamber et al. |
| 10,036,142 | B2 | 7/2018 | Bamber et al. |
| 10,053,327 | B2 | 8/2018 | Leslie et al. |
| 10,054,560 | B2 | 8/2018 | Bamber et al. |
| 10,259,015 | B2 | 4/2019 | Bamber et al. |
| 10,450,172 | B1 | 10/2019 | Shaui |
| 10,493,494 | B2 | 12/2019 | Bamber et al. |
| 10,857,568 | B2 | 12/2020 | Bamber et al. |
| 10,982,414 | B2 | 4/2021 | Bamber et al. |
| 11,066,048 | B2 | 7/2021 | Gu et al. |
| 11,219,927 | B2 | 1/2022 | Bamber et al. |
| 11,247,240 | B2 | 2/2022 | Bamber et al. |
| 11,247,241 | B2 | 2/2022 | Bamber et al. |
| 2003/0009286 | A1 | 1/2003 | Shibusawa |
| 2004/0066890 | A1 | 4/2004 | Dalmijn et al. |
| 2005/0002029 | A1 | 1/2005 | Gornushkin et al. |
| 2005/0150141 | A1 | 7/2005 | Suzik |
| 2005/0150844 | A1 | 7/2005 | Hyndman |
| 2005/0242006 | A1 | 11/2005 | Bohlig |
| 2006/0090379 | A1 | 5/2006 | Furem |
| 2006/0171504 | A1 | 8/2006 | Sommer et al. |
| 2007/0030953 | A1 | 2/2007 | Sommer et al. |
| 2007/0295590 | A1 | 12/2007 | Weinberg |
| 2008/0047170 | A1 | 2/2008 | Nichols |
| 2008/0192987 | A1 | 8/2008 | Helgason et al. |
| 2009/0076674 | A1 | 3/2009 | Kiegeral et al. |
| 2009/0256412 | A1 | 10/2009 | Nieto et al. |
| 2009/0322357 | A1 | 12/2009 | Beaulieu |
| 2010/0005926 | A1 | 1/2010 | Valerio |
| 2010/0091103 | A1 | 4/2010 | Peltonen et al. |
| 2011/0066404 | A1 | 3/2011 | Salazar-Tio et al. |
| 2011/0168962 | A1 | 7/2011 | Yang et al. |
| 2011/0186660 | A1 | 8/2011 | Harding et al. |
| 2011/0313625 | A1 | 12/2011 | Miller et al. |
| 2012/0033212 | A1 | 2/2012 | Barefield |
| 2012/0046983 | A1 | 2/2012 | Nettleton et al. |
| 2012/0148018 | A1 | 6/2012 | Sommer, Jr. |
| 2013/0026263 | A1 | 1/2013 | Bamber et al. |
| 2013/0098807 | A1 | 4/2013 | Wellwood et al. |
| 2013/0126399 | A1 | 5/2013 | Wolff |
| 2013/0137944 | A1* | 5/2013 | Jeong ............... A61B 5/0068 600/431 |
| 2013/0169961 | A1 | 7/2013 | Kraft |
| 2013/0201481 | A1 | 8/2013 | Bamber et al. |
| 2013/0272829 | A1 | 11/2013 | Innes et al. |
| 2013/0292307 | A1 | 11/2013 | Bamber et al. |
| 2013/0313169 | A1 | 11/2013 | Lapeyre et al. |
| 2013/0346127 | A1 | 12/2013 | Jensen |
| 2014/0088876 | A1 | 3/2014 | Shiley et al. |
| 2014/0112749 | A1 | 4/2014 | Doll et al. |
| 2014/0144342 | A1 | 5/2014 | Bye |
| 2014/0200054 | A1 | 7/2014 | Fraden |
| 2014/0225416 | A1 | 8/2014 | Harding et al. |
| 2014/0260801 | A1 | 9/2014 | Wellwood et al. |
| 2015/0004574 | A1 | 1/2015 | Bomer |
| 2015/0051498 | A1* | 2/2015 | Darty ............... G01J 3/2803 600/407 |

(56) References Cited

U.S. PATENT DOCUMENTS

| | | | |
|---|---|---|---|
| 2015/0085123 A1 | 3/2015 | Tafazoli | |
| 2015/0108258 A1 | 4/2015 | Bamber et al. | |
| 2015/0122705 A1 | 5/2015 | Latti | |
| 2015/0343999 A1 | 12/2015 | Lopez Galera et al. | |
| 2016/0016202 A1* | 1/2016 | Bamber | G01N 33/24 |
| | | | 37/444 |
| 2016/0054044 A1 | 2/2016 | Jeong et al. | |
| 2016/0088240 A1 | 3/2016 | Kostrzewa et al. | |
| 2016/0103316 A1 | 4/2016 | Rousseau | |
| 2016/0107197 A1 | 4/2016 | Hartmann | |
| 2016/0299116 A1 | 10/2016 | Talmaki | |
| 2017/0037594 A1 | 2/2017 | Wada | |
| 2017/0121945 A1 | 5/2017 | Bamber et al. | |
| 2017/0239693 A1 | 8/2017 | Nabavi | |
| 2019/0041234 A1 | 2/2019 | Ghannam | |
| 2019/0071845 A1 | 3/2019 | Lindskov | |
| 2019/0376158 A1* | 12/2019 | Buffington | C22B 3/12 |
| 2020/0123732 A1 | 4/2020 | Hall et al. | |
| 2020/0230659 A1 | 7/2020 | Nabavi | |
| 2020/0276593 A1* | 9/2020 | Mueller | B02C 17/1805 |
| 2021/0260628 A1 | 8/2021 | Bamber et al. | |
| 2021/0340733 A1* | 11/2021 | Bamber | E02F 9/264 |
| 2023/0003918 A1* | 1/2023 | Job | G01N 21/359 |
| 2023/0160727 A1 | 5/2023 | Thomsson et al. | |
| 2023/0243650 A1 | 8/2023 | Thomsson et al. | |
| 2023/0260153 A1* | 8/2023 | Saric | G01S 17/894 |
| | | | 382/103 |
| 2024/0054766 A1* | 2/2024 | Yu | G06V 10/14 |
| 2024/0255350 A1* | 8/2024 | Taniguchi | G01J 3/027 |

FOREIGN PATENT DOCUMENTS

| | | |
|---|---|---|
| CA | 2840545 | 1/2013 |
| CN | 108017002 | 5/2018 |
| CN | 111391791 | 7/2020 |
| CN | 112246777 | 1/2021 |
| CN | 216711399 | 6/2022 |
| DE | 3228447 | 4/1986 |
| EP | 2141414 | 1/2010 |
| FR | 765387 | 6/1934 |
| GB | 2188727 | 10/1987 |
| JP | S5389701 | 7/1978 |
| JP | S62202131 | 9/1987 |
| JP | H0742201 | 2/1995 |
| KR | 101402667 | 6/2014 |
| WO | WO9530880 | 1/1995 |
| WO | WO9922870 | 5/1999 |
| WO | WO2005085968 | 2/2006 |
| WO | WO2008046136 | 4/2008 |
| WO | WO2008129115 | 10/2008 |
| WO | WO2009076674 | 6/2009 |
| WO | WO2010028446 | 3/2010 |
| WO | WO2011116417 | 9/2011 |
| WO | WO2011120086 | 10/2011 |
| WO | WO2011134009 | 11/2011 |
| WO | WO2011150464 | 12/2011 |
| WO | WO2013001364 | 1/2013 |
| WO | WO2013016774 | 2/2013 |
| WO | WO2013033572 | 3/2013 |
| WO | WO2013163756 | 11/2013 |
| WO | WO2016008059 | 1/2016 |
| WO | 2018231070 | 12/2018 |
| WO | 2021119813 | 6/2021 |

OTHER PUBLICATIONS

Examination Report for European Patent Application No. 20165382.1, mailing date Apr. 3, 2023, 6 pages.
Extended European Search Report for European Patent Application No. 23175505.9, mailed Jun. 16, 2023, 7 pages.
International Search Report and Written Opinion for International Application No. PCT/CA22/51717, mailed Mar. 14, 2023, 10 pages.
International Search Report and Written Opinion for International Application No. PCT/CA22/51718, mailed Mar. 14, 2023, 12 pages.
International Search Report and Written Opinion for International Application No. PCT/CA23/50142, mailed May 25, 2023, 6 pages.
Job et al., "Real-time shovel-mounted coal or ore sensing." Proceedings of the AusIMM Iron Ore Conference, 2017, pp. 397-406.
Bamber, Andrew Sherliker, "Integrated Mining, Pre-Construction and Waste Disposal Systems for the Increased Sustainability of Hard Rock Metal Mining," Apr. 2008, pp. 29, 37-44, 85-89. <https://circle.ubc.ca/handle/2429/779>.
Examination Report for Australian Patent Application 2012277493; mailed Jul. 8, 2016, 4 pages.
Examination Report for Australian Patent Application 2013255048; mailed Jan. 21, 2016, 3 pages.
Examination Report for Australian Patent Application 2013255051; mailed Jan. 27, 2016, 3 pages.
Examination Report for Australian Patent Application 2017201320; mailed Mar. 28, 2018, 4 pages.
Examination Report for Australian Patent Application 2020202849; mailed Jun. 10, 2021, 6 pages.
Examination Report for Australian Patent Application No. 2022202912; mailing date Jun. 17, 2022, 3 pages.
Examination Report for Australian Patent Application No. 2015292228, mailing date Oct. 4, 2017, 4 pages.
Examination Report for Australian Patent Application No. 2015292229, mailing date Apr. 3, 2018, 6 pages.
Examination Report for Australian Patent Application No. 2015292229, mailing date Oct. 13, 2017, 4 pages.
Examination Report for Australian Patent Application No. 2016216528, mailed Nov. 2, 2017, 5 pages.
Examination Report for Australian Patent Application No. 2017202941, mailed Jan. 12, 2018, 2 pages.
Examination Report for Australian Patent Application No. 2018203576, mailed Jul. 30, 2019, 7 pages.
Examination Report for Australian Patent Application No. 2018204838, mailed Aug. 8, 2019, 4 pages.
Examination Report for Australian Patent Application No. 2018214109, mailed Oct. 9, 2019, 3 pages.
Examination Report for Australian Patent Application No. 2018241197, mailed Nov. 14, 2019, 5 pages.
Examination Report for Australian Patent Application No. 2019204043, mailed May 17, 2020, 5 pages.
Examination Report for Australian Patent Application No. 2020273300; mailed Oct. 23, 2021, 5 pages.
Examination Report for Canadian Patent Application 2,840,545; mailed Mar. 23, 2016, 3 pages.
Examination Report for European Patent Application No. 15824840.1, mailed Feb. 23, 2022, 3 pages.
Examination Report for European Patent Application No. 12803664.7, mailed Apr. 8, 2019, 7 pages.
Examination Report for European Patent Application No. 13784189.6, mailed Apr. 23, 2019, 3 pages.
Examination Report for European Patent Application No. 13784899.0, mailed Jun. 20, 2017, 3 pages.
Examination Report for European Patent Application No. 15824840.1, mailed Nov. 3, 2020, 4 pages.
Examination Report for European Patent Application No. 15824840.1, mailed Nov. 6, 2019, 6 pages.
Examination Report for European Patent Application No. 15824840.1, mailed Sep. 8, 2021, 5 pages.
Examination Report for European Patent Application No. 15824911.0, mailed Jul. 18, 2019, 5 pages.
Examination Report for European Patent Application No. 18166364.2, mailed Nov. 6, 2019, 3 pages.
Examiner's Requisition for Canada Patent Application No. 2,955,636, mailed Nov. 2, 2021, 4 pages.
Examiner's Requisition for Canada Patent Application No. 2,955,693; mailed Sep. 22, 2021, 5 pages.
Extended European Search Report for European Application No. 12803664.7; mailed Feb. 10, 2016, 17 pages.
Extended European Search Report for European Application No. 13784189.6; mailed Nov. 5, 2015, 7 pages.
Extended European Search Report for European Application No. 13784899.0; mailed Jun. 10, 2016, 11 pages.

(56) References Cited

OTHER PUBLICATIONS

Extended European Search Report for European Application No. 15824911.0, mailed Jan. 31, 2018, 10 pages.
Extended European Search Report for European Application No. 20165382.1; mailed Jul. 27, 2020, 9 pages.
Extended European Search Report for European Patent Application No. 15824840.1, mailed Mar. 8, 2018, 5 pages.
Extended European Search Report for European Patent Application No. 18166364.2, mailed Jul. 10, 2018, 6 pages.
Extended European Search Report for European Patent Application No. 20160983.1, mailed Oct. 2, 2020, 7 pages.
First Office Action in Chilean Patent Application No. 2017-00150; mail date Jun. 20, 2018, 7 pages.
First Office Action in Chinese Patent Application 201580050856.21; mail date May 3, 2018, 23 pages, with English translation.
First Office Action in Chinese Patent Application 201580050857.7; mail date Dec. 5, 2018, 9 pages, with English translation.
First Office Action in Chinese Patent Application 201910037844.6; mail date Sep. 27, 2020, 11 pages.
First Official Action in Chilean Patent Application 2924-2014, Mail Date Oct. 29, 2014, 5 pages.
First Official Action in Chilean Patent Application 2925-2014, Mail Date Oct. 29, 2014, 5 pages.
International Search Report and Written Opinion for International Application No. PCT/CA2013/050330, Mailed Jul. 24, 2013, 9 pages.
International Search Report and Written Opinion for International Application No. PCT/CA2013/050336, mailing date Aug. 12, 2013, 12 pages.
International Search Report and Written Opinion for International Application No. PCT/CA2015/050683; mailed Oct. 21, 2015, 7 pages.
International Search Report and Written Opinion for International Application No. PCT/CA2015/050684, mailing date Sep. 30, 2015, 9 pages.
International Search Report and Written Opinion for International Application No. PCT/IB2012/001560, Mail Date Nov. 29, 2012, 12 pages.
Kieba et al. "Differential Soil Impediance Obstacle Detection," U.S. Department of Energy Technical Report No. DE-FC26-02NT41318, Report Issue Date Jan. 17, 2005, 72 pages.
N. G. Cutmore et al., "Ore Characterisation and Sorting," Minerals Engineering, vol. 10, No. 4., Jan. 1997, 6 pages.
Office Action in Chile Patent Application No. 00164-2017, Mail Date Apr. 5, 2018, 12 pages.
Office Action in Chile Patent Application No. 00164-2017, Mail Date Sep. 12, 2018, 15 pages.
Partial Supplementary European Search Report for European Application No. 12803664.7, Mail Date Oct. 16, 2015, 7 pages.
Partial Supplementary European Search Report for European Application No. 13784899.0, Mail Date Feb. 16, 2016, 7 pages.
Second Examination Report for Australian Patent Application 2012277493, mailing date Sep. 27, 2016, 4 pages.
Second Examination Report for Australian Patent Application No. 2018214109, mailing date Jun. 11, 2020, 3 pages.
Second Examination Report for Australian Patent Application No. 201592228, mail date Feb. 28, 2018, 4 pages.
Second Office Action for Chilean Patent Application No. 2924-2014, mail date Jan. 7, 2017, 5 pages.
Second Office Action for Chilean Patent Application No. 2925-2014, mail date Feb. 25, 2017, 5 pages.
Second Office Action in Chilean Patent Application No. 2017-00150; mail date Feb. 13, 2019, 7 pages.
Second Office Action in Chinese Patent Application 201580050857.7; mail date Jul. 31, 2019, 8 pages.
Singh et al., "Application of image processing and radial basis neural network techniques for ore sorting and ore classification," Minerals Engineering, vol. 18, Jan. 2005, 9 pages.
Supplementary European Search Report for European Application No. 12803664.7 mailed Feb. 10, 2016, 11 pages.
Supplementary European Search Report for European Application No. 13784899.0; mailed Feb. 16, 2016, 7 pages.
Third Examination Report for Australian Patent Application 2012277493; mailed Mar. 3, 2017, 4 pages.
Third Examination Report for Australian Patent Application No. 2018214109, mailed Oct. 1, 2020, 5 pages.
Third Office Action in Chinese Patent Application 201580050857.7; mail date May 29, 2020, 4 pages.
Yang et al., "Electromagnetic conductivities of rock cores: Theory and analog results," Geophysics, vol. 62, No. 6, Nov.-Dec. 1997, 15 pages.
International Search Report and Written Opinion for International Application No. PCT/CA2023/051079, mailed Oct. 31, 2023, 8 pages.
International Search Report and Written Opinion for International Application No. PCT/CA23/51078, mailed Oct. 22, 2023, 9 pages.

* cited by examiner

COMPOSITIONAL MULTISPECTRAL AND HYPERSPECTRAL IMAGING SYSTEMS FOR MINING SHOVELS AND ASSOCIATED METHODS

CROSS-REFERENCE TO RELATED APPLICATIONS

The present application claims the benefit of U.S. Provisional Patent Application No. 63/282,087, filed Nov. 22, 2021, which is incorporated herein by reference in its entirety.

TECHNICAL FIELD

The present disclosure generally relates to mining detection systems having imaging systems and, in particular embodiments, to compositional multispectral and/or hyperspectral imaging systems positioned on mining equipment to classify ore and waste minerals at the mining site and associated methods and systems.

BACKGROUND

Mineral sorting is typically undertaken by one or more sorting machines in a single stage at a facility separate from the mining site that has sensor arrays controlling a matched array of diverters. Matched sensor/diverter arrays are typically positioned with respect to an ore transport mechanism (e.g., vibrating feeder, belt conveyor, free-fall type), which moves the material to be sorted past the sensors and through the diverters that sort the material into separate streams (e.g., an "accept" or "reject" stream).

Sorting machine capacity is limited by several factors, including controller speed, belt or feeder width, segregation of particle size ranges, and separation of mineral composition (e.g., sulfide or oxide). The mineral composition dictates the extraction process required to optimize ore recovery. For example, sulfide ores are transported to flotation circuits, while oxide ores are transported to leaching circuits. Thus, if the sorting process inaccurately diverts ore to the wrong processing circuit based on mineral composition, the value of the ore is diminished, which reduces the efficiency of the circuit.

BRIEF DESCRIPTION OF THE DRAWINGS

Many aspects of the present disclosure can be better understood with reference to the following drawings. The components in the drawings are not necessarily to scale. Instead, emphasis is placed on clearly illustrating the principles of the present disclosure.

DETAILED DESCRIPTION

Disclosed herein are various embodiments of compositional imaging systems for mining shovels including multispectral imaging (MSI) and/or hyperspectral imaging (HSI) units, methods of sorting material using a mining shovel with compositional MSI and/or HSI units, and systems incorporating compositional MSI and/or HSI units at a mining site. In some embodiments disclosed herein, the mining shovels include a bucket having an MSI system with one or more spectroscopy heads (also referred to as an "MSI head assembly" or "head assembly"), each housing an MSI camera unit, a lighting unit, and a sensor generally positioned near an inlet of the bucket (e.g., the opening of the bucket in which material enters the bucket cavity). The MSI camera unit has a field of view in which the MSI camera unit captures images of mining material prior to, during, and/or after loading the mining material into the bucket. The MSI camera unit can include a lighting unit to capture images of the mining material with or without flash. The lighting unit can be spaced apart from the MSI camera unit and illuminate an irradiation region, which at least partially overlaps with the field of view of the MSI camera unit. The sensor can detect characteristics of the mining material in the field of view. The MSI heads can be in communication with a control component (e.g., one or more controllers, also referred to as "processing units") mounted to the bucket and/or remote from the bucket and can receive and/or analyze the data collected by the MSI heads.

In some embodiments, one or more processing unit is used to identify the mineral composition of the ore and/or other mining material entering the bucket of the mining shovel. In some embodiments, the MSI heads can be positioned adjacent to one or more sensors that detect characteristics and/or properties of the bucket contents, e.g., including X-Ray Fluorescence (XRF) emitters, XRF detectors, laser distance sensors, ultrasonic distance sensors, lidar distance sensors, other multi-spectral imaging sensors, other flash tubes, hyperspectral imaging cameras, hyperspectral point spectrometers, stereoscopic cameras, radiation detectors, electromagnetic detectors, gamma-ray source sensors, and the like. The sensors can be positioned on a side wall of the bucket, on an upper wall portion of the bucket, adjacent to the MSI heads, between the MSI heads, and/or at other suitable sensor locations, and can be used in conjunction with the MSI heads to identify the mineral composition and improve the grade prediction of the ore and/or other mining material entering the bucket and/or positioned within the bucket. In some embodiments, any number of MSI heads can be used with any number of sensors. In some embodiments, the MSI heads described herein can be used, either in conjunction with the MSI heads positioned at the bucket or independently, for sensing mining material composition on a conveyor belt for carrying ore. Sorting the mineral composition at the mine face during digging reduces sorting operation costs by eliminating additional sorting machines and allowing an operator to make ore and/or other mining material routing decisions at the mine face and optimize the downstream extraction process.

The mining shovels with compositional MSI and/or HSI can be part of a system used in field operations (e.g., at a mining site) to direct where material located in the bucket should be transported. In addition to the bucket described above, the system can include additional signal processing equipment located remote from the bucket, such as in the chassis of the mining shovel, and communications links between the signal processing equipment in the bucket and the signal processing equipment in the chassis. In this manner, data can be relayed from the bucket to the chassis, where, for example, further data analysis can be carried out. The system can further include an operator's enterprise resource planning (ERP) system, a fleet management system, and/or communications links for transmitting information between all of the components of the system. In some embodiments, predetermined values relating to identification of material composition is stored in a database that is part of the ERP system, such that data transmitted to the ERP system from the bucket and/or chassis can be compared against the database to match patterns and thereby identify material composition. Once material composition is identified, signals can be sent from the ERP system to the fleet management system so that a determination of where to transport the material in the bucket can be made. In other embodiments, the material composition information is sent by the signal processing equipment to the fleet management system. The decision made by the fleet management system can subsequently be communicated to, for example, a local display located in the chassis of the mining shovel so that a shovel operator can deposit the bucket material in the appropriate location.

In some embodiments, a method of in-mine sensing and classification generally includes collecting imaging data of material in a mining shovel bucket using one or more MSI heads carried by the bucket and transmitting the data obtained from sensing the material to signal processing equipment. The method can further include identifying the composition of the material by processing the data with image processing equipment. In some embodiments, the method can further include sensing, by the sensors, additional characteristics of the received material to augment the material composition identification by the data provided by the MSI heads and determine further classification of the composition of the material. Once identified, the method can further include transmitting instructions of where to transport the bucket material, such as to a mining shovel operator. Destination instructions can also be sent to a haul truck that receives the material from the mining shovel and/or to other operators in the mining ecosystem remote from the mining shovel or mining site.

Specific details of several embodiments of the present technology are described herein with reference to FIGS. 1-7. The present technology, however, can be practiced without some of these specific details. In some instances, well-known structures and techniques often associated with mining detection systems, compositional MSI, and the like, have not been shown in detail so as not to obscure the present technology. Moreover, although many of the embodiments are described below with respect to systems and methods for identifying specific materials (e.g., sulfides and oxides) and/or systems and methods mounted to a mining shovel bucket, other applications and other embodiments in addition to those described herein are within the scope of the technology. Further, although many of the embodiments are described below with respect to systems and methods that use compositional MSI, the systems and methods can utilize HSI and components thereof (e.g., hyperspectral infrared point spectrometers) and/or color cameras (e.g., RGB cameras) in place of or in addition to the MSI components disclosed herein.

The terminology used in the description presented below is intended to be interpreted in its broadest reasonable manner, even though it is being used in conjunction with a detailed description of certain specific embodiments of the invention. Certain terms may even be emphasized below; however, any terminology intended to be interpreted in any restricted manner will be overtly and specifically defined as such in this Detailed Description section.

The accompanying FIGS. 1-7 depict embodiments of the present technology and are not intended to be limiting of its scope. The sizes of various depicted elements are not necessarily drawn to scale, and these various elements can be arbitrarily enlarged to improve legibility. Component details can be abstracted in the Figures to exclude details such as position of components and certain precise connections between such components when such details are unnecessary for a complete understanding of how to make and use the present technology. Many of the details, dimensions, angles, and other features shown in the Figures are merely illustrative of particular embodiments of the disclosure. Accordingly, other embodiments can have other details, dimensions, angles, and features without departing from the spirit or scope of the present technology.

Figure 1:
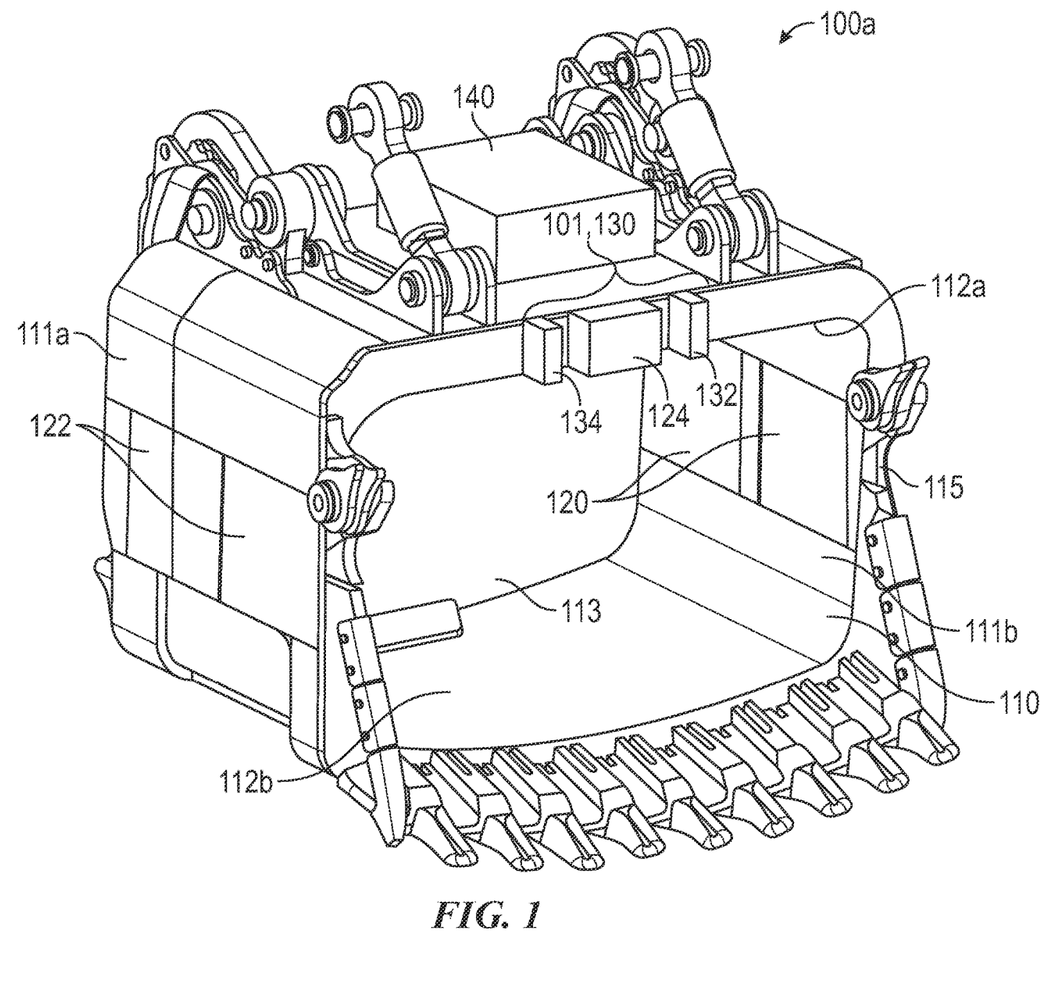
FIG. 1 is a perspective view of a mining detection system configured in accordance with embodiments of the present technology.

FIG. 1 is a perspective view of a mining detection system 100a ("system 100a") including a mining shovel bucket 110 ("bucket 110") carrying a compositional MSI system 101 ("MSI system 101") configured in accordance with embodiments of the present technology. The bucket 110 can include a plurality of walls that form an open container having an interior volume in which mining material can be received and retained, and one or more sensors positioned to detect characteristics of material as it enters and/or when it is retained within the interior volume of the bucket 110. The MSI system 101 can include at least one MSI head assembly 130, which includes an MSI camera unit 132 and a lighting unit 134 positioned such that the MSI camera unit 132 can capture data from mining material entering or positioned within the cavity of the bucket 110. The bucket 110 can include a control enclosure 140, explained in greater detail below, that is operably coupled to components of the system 100a, for example, the sensors, the MSI system 101, and/or other electrical components.

In the illustrated embodiment, the bucket 110 includes a first side wall 111a, a second side wall 111b opposite the first side wall 111a, an upper wall 112a, a lower wall 112b opposite the upper wall 112a, and a back wall 113 that together create the interior volume of the bucket 110. The bucket 110 may generally be any type of bucket suitable for use in mining shovel operations, including buckets of varying shapes, sizes, and materials.

The MSI system 101 can be mounted on or integrated into a portion of the bucket 110. In the illustrated embodiment, for example, the MSI system 101 is positioned on the upper wall 112a of the bucket 110. While FIG. 1 shows only one MSI head assembly 130 positioned on the upper wall 112a, the mining shovel bucket 110 can include any number of MSI head assemblies 130 positioned in various locations on the mining shovel bucket 110 (e.g., multiple MSI head assemblies 130 on the upper wall 112a (see FIG. 2), on the first and second side walls 111a and 111b, in the interior volume of the bucket 110, etc.), above the bucket (e.g., on a structure mounted to a component of the mining shovel) or in any other suitable location where the MSI system 101 can capture images of the mining material prior to or during loading of the mining material into the bucket. Further, although each MSI head assembly 130 is shown with one MSI camera unit 132 and one lighting unit 134, in some embodiments, the MSI head assembly 130 can include multiple MSI camera units per lighting unit, multiple lighting units per MSI camera unit, or multiple MSI cameras and lighting units.

In some embodiments, the mining shovel bucket 110 can further include one or more sensors positioned to detect characteristics of material as it enters and/or when it is retained within the interior volume of the bucket 110. As shown in FIG. 1, for example, the system 100a can include in-cheek sensors 120 on the first side wall 111a and an in-cheek sensor 122 on the second side wall 111b, each in-cheek sensor 120 and 122 facing inward towards the interior volume of the bucket 110 so that material entering and positioned within the interior volume can be subjected to sensing by the in-cheek sensors 120 and 122. The bucket 110 can also or alternatively include at least one peripheral sensor 124 positioned along a periphery of an inlet 115 of the bucket 110 on the upper wall 112a and facing, e.g., downward (for a down looking peripheral sensor) at the entrance to or into the interior volume so that material being loaded into or within the interior volume can be subjected to sensing by the peripheral sensor 124, outward so that material on the mining face can be subject to sensing by the peripheral sensor 124, etc. The in-cheek sensors 120 and 122 and the peripheral sensor 124 can be any type of sensor suitable for use in analyzing and collecting data on mining material that can subsequently be used in determining the composition of the mining material. For example, the in-cheek sensors 120 and 122 and the peripheral sensor 124 can be radiometric sensors, photometric sensors, and/or electromagnetic sensors, e.g., the sensors shown and described in U.S. Pat. Nos. 9,522,415, 10,036,142, and 10,982,414, each titled MINING SHOVEL WITH COMPOSITIONAL SENSORS, which are incorporated by reference herein in their entirety. In some embodiments, the system 100a can include a greater number of in-cheek sensors and/or down looking sensors than shown in FIG. 1, and/or one or more of the in-cheek sensors and/or down looking sensors may be omitted. The sensors may be housed within and/or encapsulated by a ruggedized, non-metallic material such as one of vulcanized rubber or other rugged, non-conductive elastomeric material, that does not interfere with the operation of the sensor, yet provides a robust housing to protect the sensors from the rugged mining environment (e.g., hard, heavy materials being scooped within the bucket 110).

Figure 2:
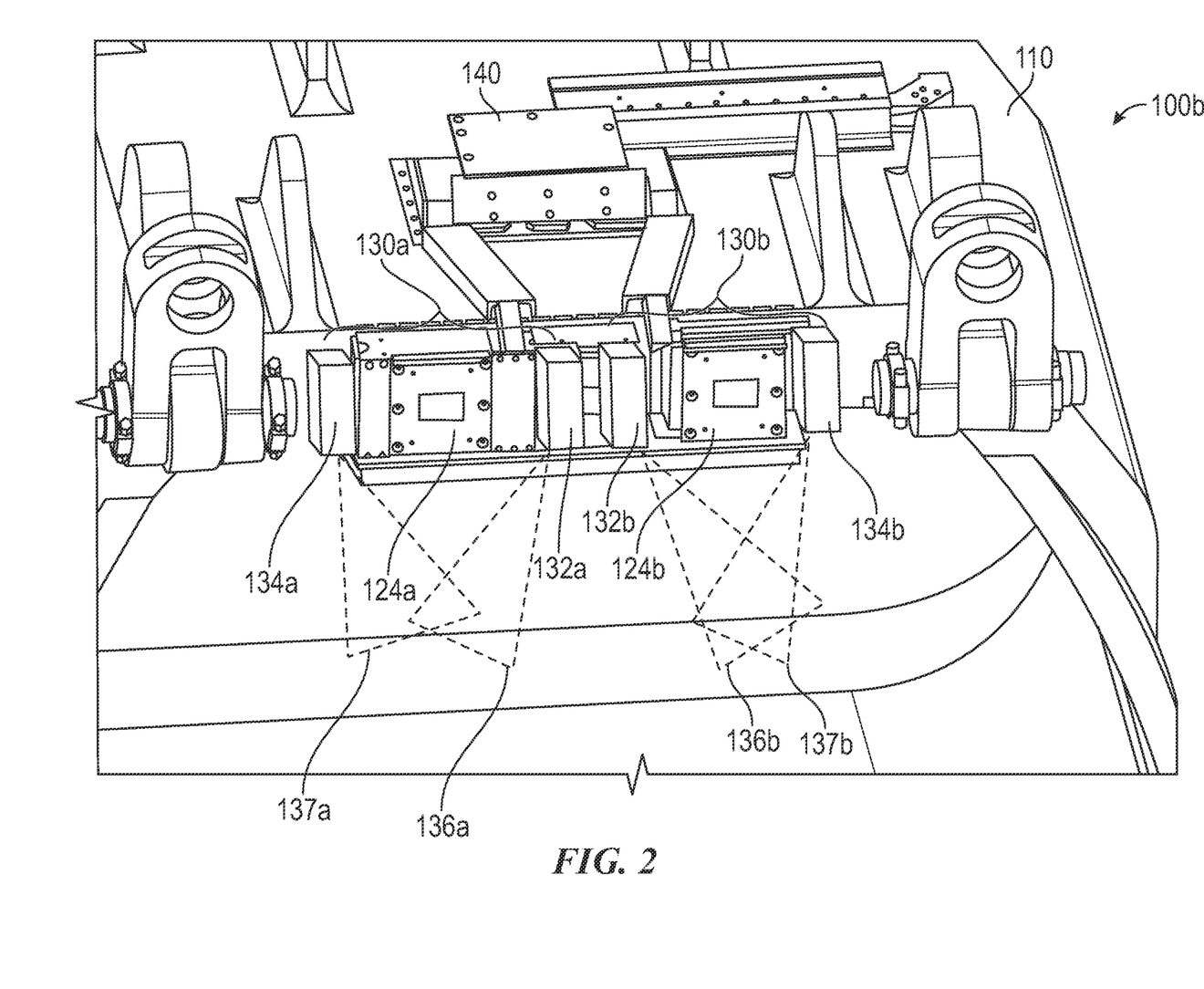
FIG. 2 is an enlarged perspective view of a compositional multispectral imaging system of the mining detection system of FIG. 1 configured in accordance with embodiments of the present technology.

FIG. 2 is a perspective view of a system 100b configured in accordance with embodiments of the present technology. In the illustrated embodiment, the system 100b includes a first MSI head assembly 130a having a first MSI camera unit 132a and an associated a first lighting unit 134a, and a second MSI head assembly 130b having a second MSI camera unit 132b and an associated second lighting unit 134b. As shown in FIG. 2, a first peripheral sensor 124a can be positioned between the first MSI camera unit 132a and the first lighting unit 134a, and a second peripheral sensor 124b can be positioned between the second MSI camera unit 132b and the second lighting unit 134b. Embodiments with sensors positioned between the MSI head components allow the MSI camera and the sensor to gather data from the same portion of ore and/or other mining material entering or in the bucket 110 and correlate data for the same portion of ore. Positioning the down looking sensors between the MSI head components can allow a more dynamic grade model capable of compensating for changes in sulfide concentration. For example, copper content contained in sulfide materials (as opposed to oxide materials) may be underestimated with data gathered only by the down looking sensors, but using the sensor data in conjunction with the imaging data from the MSI heads 130a and 130b can compensate for changes in sulfide concentration. In some embodiments, an XRF sensor is used to determine the percent of copper in the mining material. In some embodiments, one or both of the peripheral sensors 124a and 124b can be omitted, the system 101 can include additional sensors, and/or sensors can be spaced apart from the MSI camera units 132a and 132b.

Each MSI camera unit 132 has a field of view 136 (identified individually as a first field of view 136a and a second field of view 136b) and the associated lighting unit 134 has an irradiation region 137 (identified individually as a first irradiation region 137a and a second irradiation region 137b) directed such that at least a portion of the field of view 136 and the irradiation region 137 overlap with each other such that the lighting unit 134 illuminates the region in which the MSI camera unit 132 takes image data to enhance image quality and/or allow for image capture in dark environments. In the embodiment illustrated in FIG. 2, for example, the first camera field of view 136a of the first MSI camera unit 132a and the first irradiation region 137a are directed toward each other to a central region between the first MSI camera unit 132a and the first lighting unit 134a, and generally aligned with the data capture area of the first peripheral sensor 124a. Similarly, the second camera field of view 136b of second MSI camera unit 132b and the second irradiation region 137b are directed toward a region between the second MSI camera unit 132b and the second lighting unit 134b, and generally aligned with the data capture area the second peripheral sensor 124b. In some embodiments, for example, the field of view 136 of each MSI camera unit 132 and the corresponding illumination region 137 can be directed downwardly, into the interior compartment of the bucket 110, and the peripheral sensor 124 can be a downward looking sensor directed to the same or overlapping region. In some embodiments, each MSI camera unit 132 and lighting unit 134 pair can be spaced apart from each other, rather than adjacent to each other, to provide for specific lighting characteristics, avoid the light from causing the direct capture of dust and other debris during imaging by the MSI camera unit 132, and/or allow a sensor to be positioned therebetween. For example, the MSI camera unit 132 and the lighting unit 134 can be spaced apart by 500 mm to 800 mm. In some embodiments, the MSI camera unit 132 captures images without a flash. In some embodiments, the lighting unit is configured to emit a flash to provide a lighting environment for consistent data collection. In some embodiments, the lighting unit is configured to emit a constant light source to provide a consistent lighting environment for consistent data collection.

Referring to FIGS. 1 and 2 together, the systems 100a and 100b can further include the control enclosure 140 (also referred to as a "control component") operably coupled to components of the MSI system 101, the sensors 120, 122, and 124, and/or other electrical components that collect data associated with the mined material as it enters the bucket 110 and/or when it is retained within the bucket 110. The control enclosure 140 can be mounted to a surface of the bucket 110 (e.g., an exterior surface outside of the bucket cavity) or remote from the bucket 110. In the illustrated embodiments, for example, the control enclosure can be mounted to a top exterior surface of the upper wall 112a. The size, shape, and material of the enclosure 140 is generally not limited, and can be selected such that it safely accommodates and protects the various electronics that resides therein. The control enclosure 140 can house or otherwise carry image processing components, signal processing components, communication components, memory components, and/or a wide variety of other or additional components used in carrying out partial or complete processing of imaging data and/or sensor data received from the MSI system 101 and/or the sensors 120, 122, and 124 and/or transmit that data. For example, image and signal processing electronics of the control enclosure 140 can receive image data and signals from the MSI system 101 and/or the sensors 120, 122, and 124, and partially or fully process the image data and/or signals to identify the composition of the mining material loaded in the bucket 110. The communications components can then transmit signals including the processed data from the bucket 110 to locations remote to the bucket 110 (e.g., to the chassis of the mining shovel, haul trucks, mobile devices, remote stations on the mining operation field). In some embodiments, the communications components housed in the enclosure 140 are wireless communications components that wirelessly deliver signals to transmit the processed data and/or associated information. In a situation where wireless communications are lost, the enclosure 140 can continue to operate independently and resume data communication when the connection is restored. The enclosure 140 can further house imaging, lighting, and/or sensor electronics that are part of the MSI camera units 132, the lighting units 134, and/or the sensors 120, 122, and 124. The enclosure 140 can draw power from the mining shovel machine and/or include on-board power components (e.g., batteries, solar power) for powering the various MSI camera units 132, lighting units 134, sensors 120, 122, and 124, image and signal processing equipment, communication components, and the like. In some embodiments, the MSI system described herein can be used, either in conjunction with the MSI system positioned at the bucket or independently, at a location different from the bucket. For example, in some embodiments, the MSI system can be used for sensing mining material composition on a conveyor belt for carrying ore. In other embodiments, the MSI system described herein can be used for sensing mining material composition on an in-pit hopper that helps optimize the loading of hauling trucks.

Figure 3:
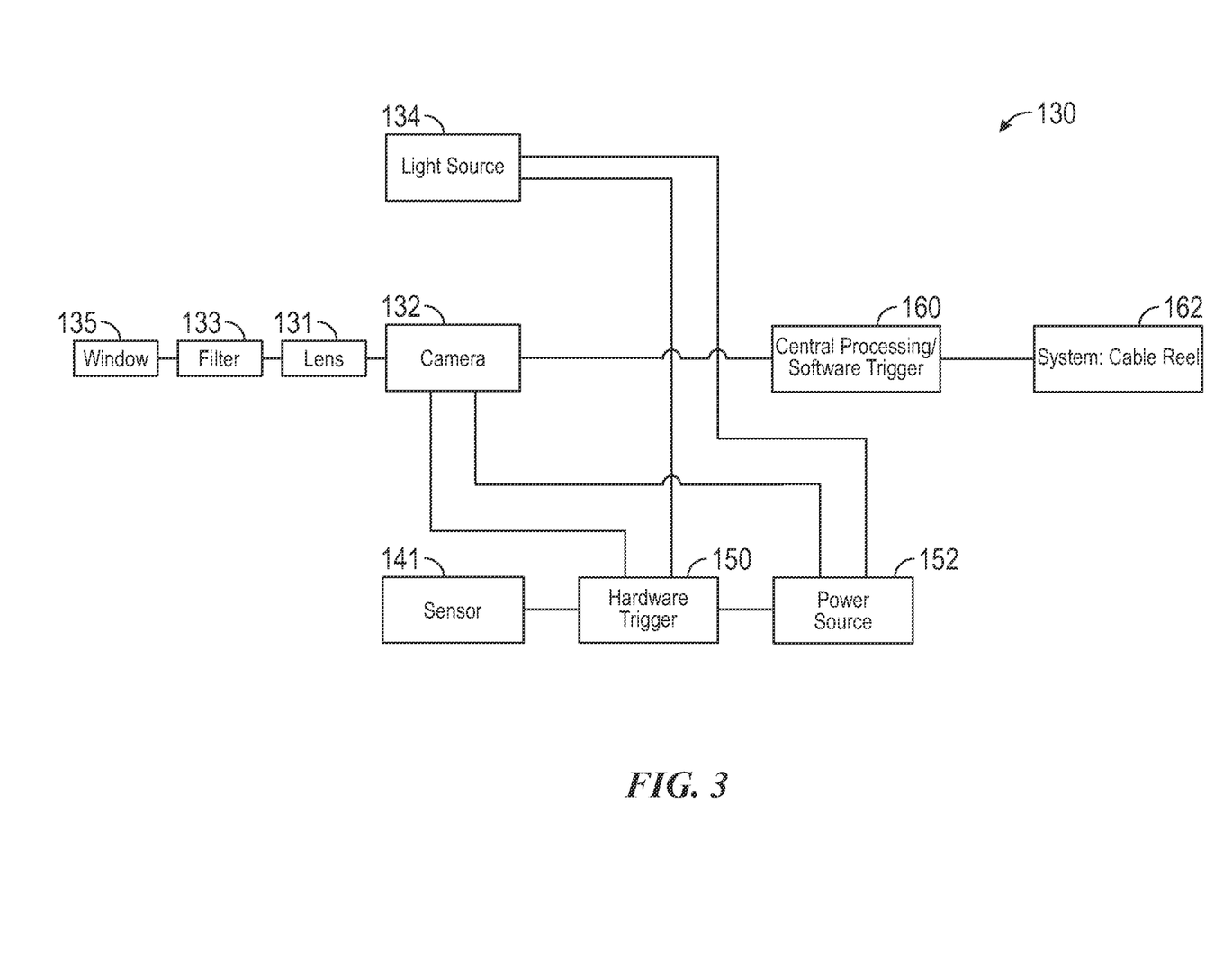
FIG. 3 is a block diagram of a compositional multispectral imaging system configured in accordance with embodiments of the present technology.

FIG. 3 is a block diagram showing additional details of one of the MSI head assemblies 130 of the MSI system 101 of FIGS. 1 and 2 configured in accordance with embodiments of the present technology. The MSI head assembly 130 includes the MSI camera unit 132 and the lighting unit 134. The MSI camera unit 132 can include a lens 131 to focus the image on the sensor of the MSI camera unit 132, and a band pass filter 133 positioned over the lens 131 to provide the proper spectral range for the MSI camera unit 132. The filter 133 and the lens 131 can be protected by dirt and debris with a window 135. In some embodiments, the window 135 can be a self-cleaning window, e.g., the self-cleaning windows shown and described in U.S. Provisional Patent Application No. 63/281,929, filed Nov. 22, 2021, and titled SELF-CLEANING SENSOR WINDOW AND ASSOCIATED SYSTEMS AND METHODS, which is appended hereto in Appendix A. The head assembly 130 can further include a hardware trigger 150 configured to actuate the MSI camera unit 132 and the lighting unit 134 based on input from a proximity sensor 141 (e.g., a laser, see FIG. 4) that is configured to detect the distance between the MSI camera unit 132 and the mining material. Further, a central processing unit 160 can be in communication with the MSI camera unit 132 and the lighting unit 134 to provide a software trigger to actuate the MSI camera unit 132 and the lighting unit 134, e.g., by an operator input, by instructions from the software, at a set interval, etc. The central processing unit 160 can be in communication with the system of the mining shovel 162 through a cable reel, other communication line, and/or a wireless connection. The head assembly 130 can further include a power source 152 operably coupled to the various system components (e.g., the hardware trigger 150, the MSI camera unit 132, the lighting unit 134, and the like) and configured to provide power to these components. The components of the head assembly 130 can be housed within a single housing, spaced apart from each other in different housings (e.g., the control enclosure 140 of FIGS. 1 and 2), and/or separate components operably connected to each other.

The lighting unit 134 can have varied light characteristics (e.g., pulsed or continuous beam, and varying spectra, illumination area, illumination intensity, and illumination distribution), and the lighting unit 134 can be triggered by the hardware trigger 150. The lighting unit 134 can be any suitable light source (e.g., xenon, halogen, incandescent, etc.), and the light source types for the lighting unit 134 may be specified based on expected durability when mounted in an environment such as the bucket 110. In some embodiments, the wavelengths of the light emitted from the lighting unit 134 can be predefined and configured to match and even extend beyond that of the MSI camera unit 132. In other embodiments, the wavelengths of light emitted from the lighting unit 134 can be predefined and configured to be of different wavelengths than that of the MSI camera unit 132. Each lighting unit 134 can include a lens and a reflector that enhance the uniformity of the illumination pattern (e.g., the illumination region 137 of FIG. 2).

During mining operations, if the proximity sensor 141 detects mining material within the depth of field (DOF) of the MSI camera unit 132 (e.g., between 1 m and 2 m of the MSI camera unit 132), the hardware trigger 150 and/or the central processing unit 160 can actuate the MSI camera unit 132 to initiate the capturing of a series of images that can be used by the image processing equipment to analyze the mining material entering or contained within the bucket 110. In some embodiments, the MSI camera unit 132 can collect images using ambient light, or can be used in conjunction with light emitted by the lighting unit 134. Images captured using ambient light can be corrected in post image processing, which may eliminate the need for a lighting unit in the MSI head assembly 130. In some embodiments, a first image is taken by the MSI camera unit 132 without light from the lighting unit 134 and near the midrange of the DOF of the MSI camera unit 132. Once the first image is taken, the lighting unit 134 can sync with the MSI camera unit 132 to capture a subsequent image with illumination and also near the midrange of the DOF of the MSI camera unit 132. Any order of image with ambient light or with illumination is also within the scope of the present technology. The image processing system can use the captured images to estimate the material composition and divide it into several categories, e.g., high oxide, low oxide, oxide absent, etc. The data from the image processing system can be used with the sensor data from additional sensors (e.g., down-looking sensors) to further classify the mining material and increase classification accuracy and determine ore-waste distinctions, such as whether the ore and/or other mining material should be processed or discarded.

Figure 4:
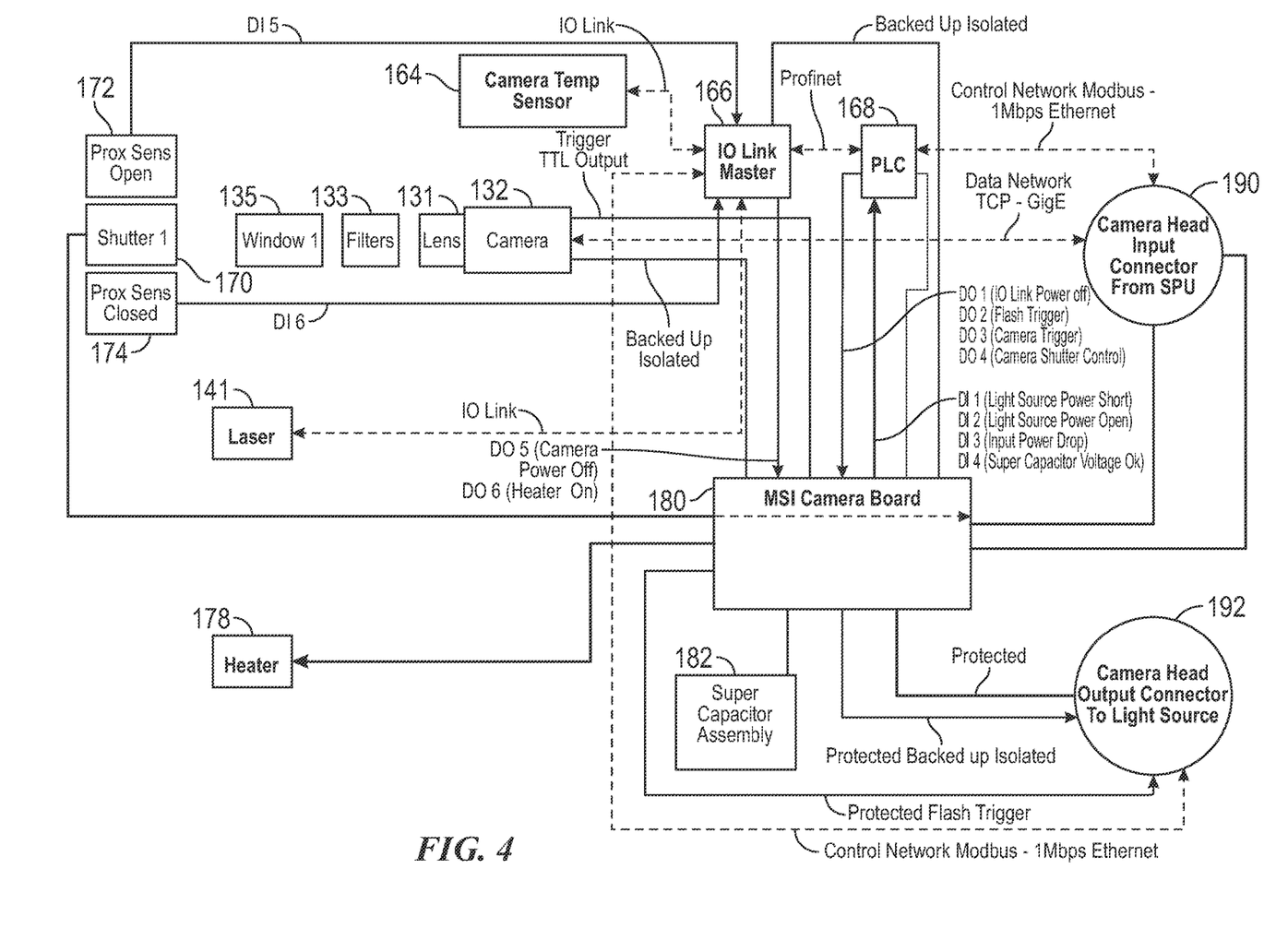
FIG. 4 is a diagram of a camera portion of the compositional multispectral imaging system of FIG. 3.

FIG. 4 is a schematic illustration of camera components of the MSI system 101 of FIGS. 1 and 2. The camera components illustrated in FIG. 4 can be housed within a single housing, spaced apart from each other in different housings (e.g., the control enclosure 140 of FIGS. 1 and 2), and/or separate components operably connected to each other. As shown in FIG. 4, the MSI camera unit 132 is in communication with an MSI camera board 180, which is in communication with a camera head input connector 190 (e.g., the image processing equipment of the control enclosure 140 of FIGS. 1 and 2) and a camera head output connector 192 to the lighting unit 132 (see FIG. 5). The MSI camera board 180 can include a super capacitor assembly 182. The MSI camera board 180 is in communication with a programmable logic controller (PLC) 168 configured to monitor the state of input devices and make decisions based upon software to control the state of output devices. The PLC 168 is in communication with an input/output (TO) link master 166 that provides a link for communication between various components of the schematic of FIG. 4. The IO link master 166 is in communication with a camera temperature sensor 164 configured to determine, for example, if the MSI camera unit 132 is below an operating temperature range. If the temperature is below an operating temperature range, the PLC 168 can send a signal through the MSI camera board 180 to a heater 178 configured to heat the MSI camera unit 132 to within the operating temperature range. The proximity sensor 141 can be used to determine if mining material is within the DOF of the MSI camera unit 132. The MSI system 101 may further include a shutter 170 in communication with the MSI camera board 180 and configured to protect the window 135, the filter 133, and the lens 131 during use. The shutter 170 can be actuated by a proximity sensor for opening 172 and a proximity sensor for closing 174.

Figure 5:
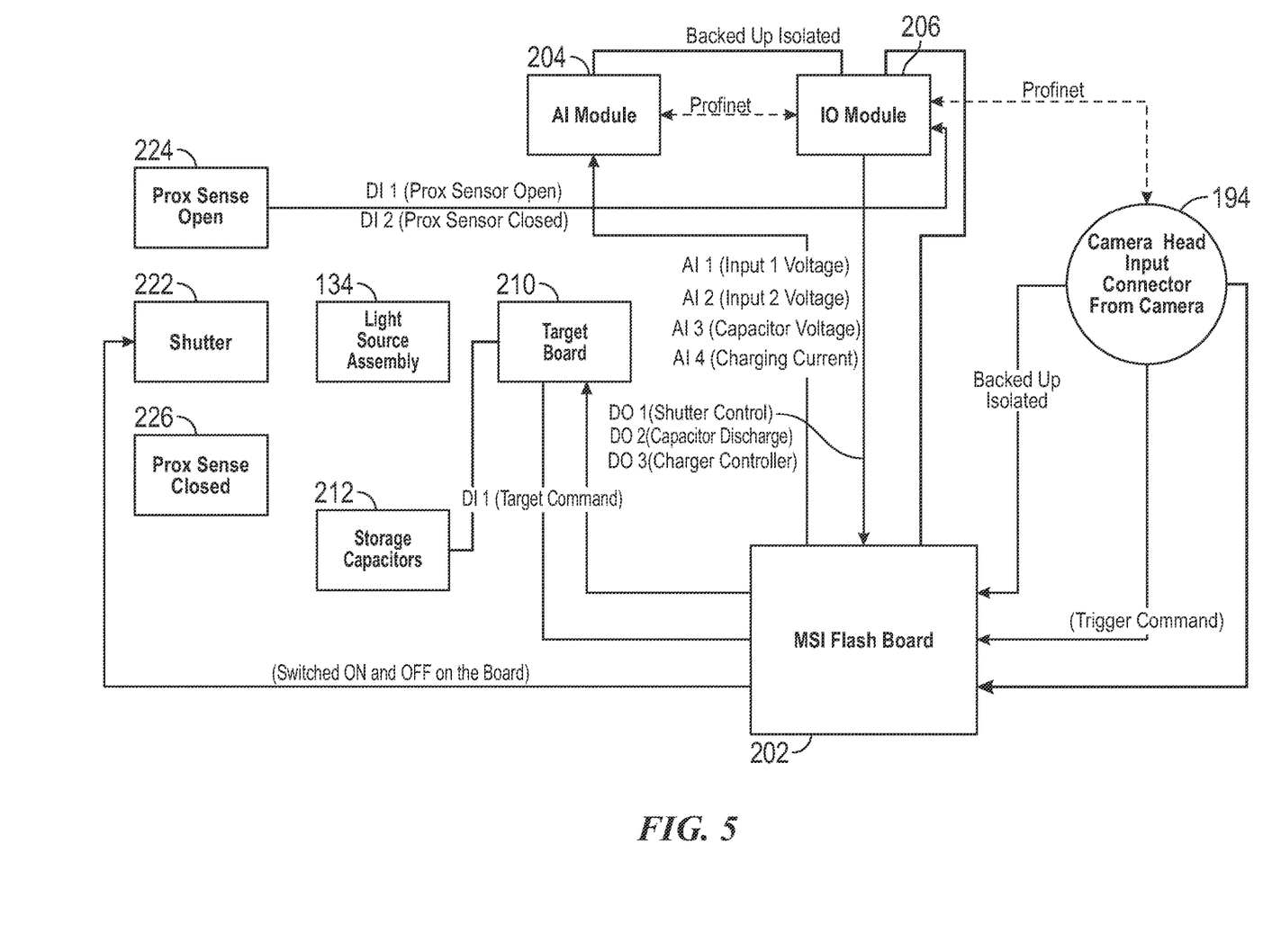
FIG. 5 is a diagram of a lighting portion of the compositional multispectral imaging system of FIG. 3.

FIG. 5 is a schematic illustration of lighting components of the MSI system 101 of FIGS. 1 and 2. The lighting components illustrated in FIG. 5 can be housed within a single housing, spaced apart from each other in different housings (e.g., the control enclosure 140 of FIGS. 1 and 2), and/or separate components operably connected to each other. As shown in FIG. 5, the lighting unit 134 is in communication with an MSI flash board 202, which is in communication with a camera head input connector 194 from the camera head output connector 192. In other embodiments, the MSI flash board 202 is in communication with the system (e.g., the image processing equipment of the control enclosure 140 of FIGS. 1 and 2). The MSI flash board 202 is in communication with an analog input (AI) module 204 and with an IO module 206 that provides a link for communication between various components of the schematic of FIG. 5. The MSI flash board 202 is in communication with a trigger board 210 having storage capacitors 212, where the trigger board 210 is configured to actuate the lighting unit 134. The MSI system 101 may further include a shutter 220 in communication with the IO module 204 and configured to protect the lighting unit 134 while not in use. The shutter 220 can be actuated by a proximity sensor for opening 222 and a proximity sensor for closing 224.

Figure 6:
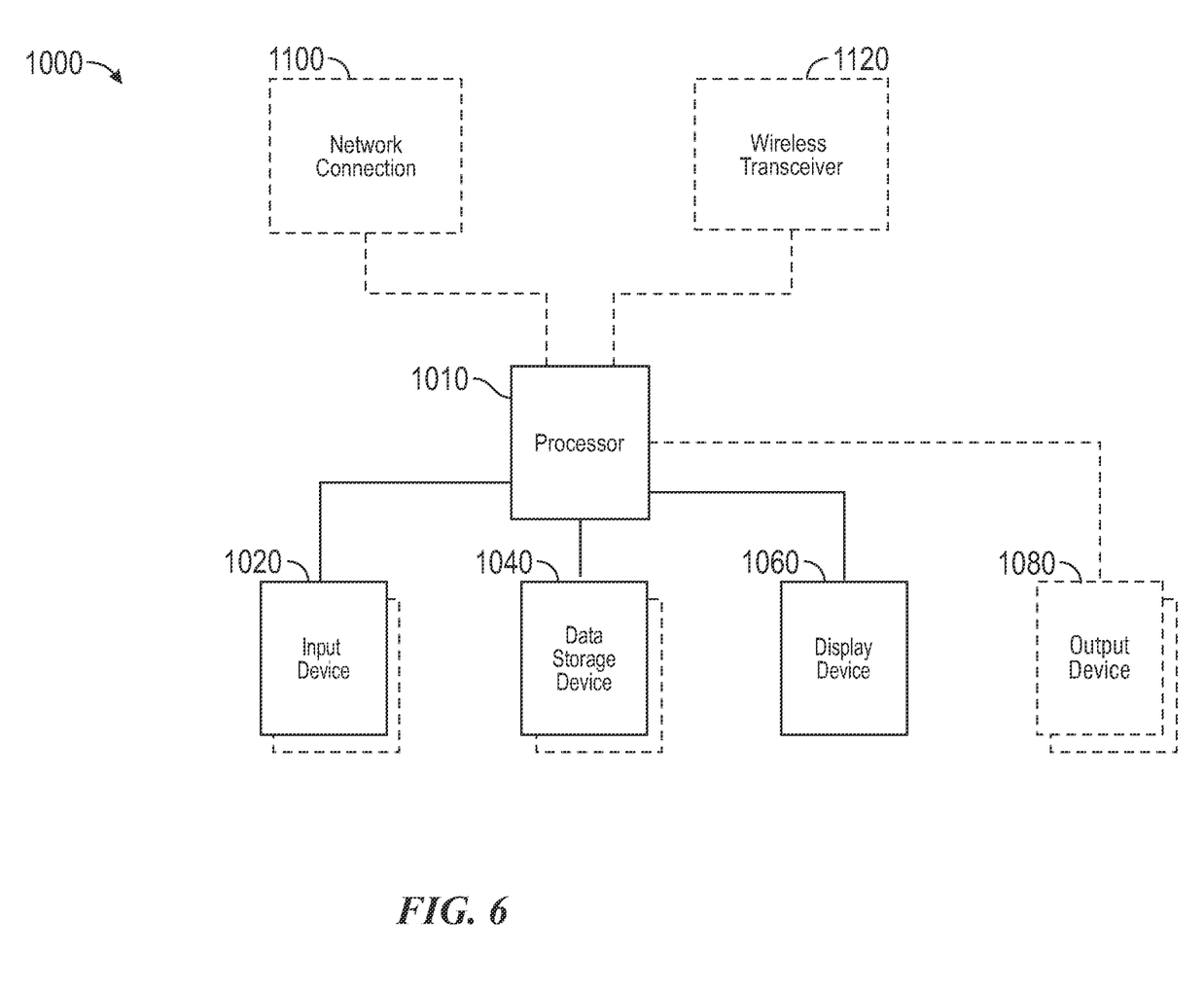
FIG. 6 is a block diagram of a suitable computer that may employ aspects of the various embodiments of the present technology.

FIG. 6 and the following discussion provide a brief, general description of a suitable computing environment in which aspects of the disclosed system can be implemented. Although not required, aspects and embodiments of the disclosed system will be described in the general context of computer-executable instructions, such as routines executed by a general-purpose computer, e.g., a server or personal computer. Those skilled in the relevant art will appreciate that the various embodiments can be practiced with other computer system configurations, including Internet appliances, hand-held devices, wearable computers, cellular or mobile phones, multi-processor systems, microprocessor-based or programmable consumer electronics, set-top boxes, network PCs, mini-computers, mainframe computers and the like. The embodiments described herein can be embodied in a special purpose computer or data processor that is specifically programmed, configured or constructed to perform one or more of the computer-executable instructions explained in detail below. Indeed, the term "computer" (and like terms), as used generally herein, refers to any of the above devices, as well as any data processor or any device capable of communicating with a network, including consumer electronic goods such as game devices, cameras, or other electronic devices having a processor and other components, e.g., network communication circuitry.

The embodiments described herein can also be practiced in distributed computing environments, where tasks or modules are performed by remote processing devices, which are linked through a communications network, such as a Local Area Network ("LAN"), Wide Area Network ("WAN") or the Internet. In a distributed computing environment, program modules or sub-routines may be located in both local and remote memory storage devices. Aspects of the system described below may be stored or distributed on computer-readable media, including magnetic and optically readable and removable computer discs, stored as in chips (e.g., EEPROM or flash memory chips). Alternatively, aspects of the system disclosed herein may be distributed electronically over the Internet or over other networks (including wireless networks). Those skilled in the relevant art will recognize that portions of the embodiments described herein may reside on a server computer, while corresponding portions reside on a client computer. Data structures and transmission of data particular to aspects of the system described herein are also encompassed within the scope of this application.

Referring to FIG. 6, one embodiment of the system described herein employs a computer 1000, such as a personal computer or workstation, having one or more processors 1010 coupled to one or more user input devices 1020 and data storage devices 1040. The computer is also coupled to at least one output device such as a display device 1060 and one or more optional additional output devices 1080 (e.g., printer, plotter, speakers, tactile or olfactory output devices, etc.). The computer may be coupled to external computers, such as via an optional network connection 1100, a wireless transceiver 1120, or both.

The input devices 1020 may include a keyboard and/or a pointing device such as a mouse. Other input devices are possible such as a microphone, joystick, pen, game pad, scanner, digital camera, video camera, and the like. The data storage devices 1040 may include any type of computer-readable media that can store data accessible by the computer 1000, such as magnetic hard and floppy disk drives, optical disk drives, magnetic cassettes, tape drives, flash memory cards, digital video disks (DVDs), Bernoulli cartridges, RAMs, ROMs, smart cards, etc. Indeed, any medium for storing or transmitting computer-readable instructions and data may be employed, including a connection port to or node on a network such as a local area network (LAN), wide area network (WAN) or the Internet (not shown in FIG. 6).

Aspects of the system described herein may be practiced in a variety of other computing environments. For example, referring to FIG. 7, a distributed computing environment with a web interface includes one or more user computers 2020 in a system 2000 are shown, each of which includes a browser program module 2040 that permits the computer to access and exchange data with the Internet 2060, including web sites within the World Wide Web portion of the Internet. The user computers may be substantially similar to the computer described above with respect to FIG. 6. User computers may include other program modules such as an operating system, one or more application programs (e.g., word processing or spread sheet applications), and the like. The computers may be general-purpose devices that can be programmed to run various types of applications, or they may be single-purpose devices optimized or limited to a particular function or class of functions. More importantly, while shown with web browsers, any application program for providing a graphical user interface to users may be employed, as described in detail below; the use of a web browser and web interface are only used as a familiar example.

Figure 7:
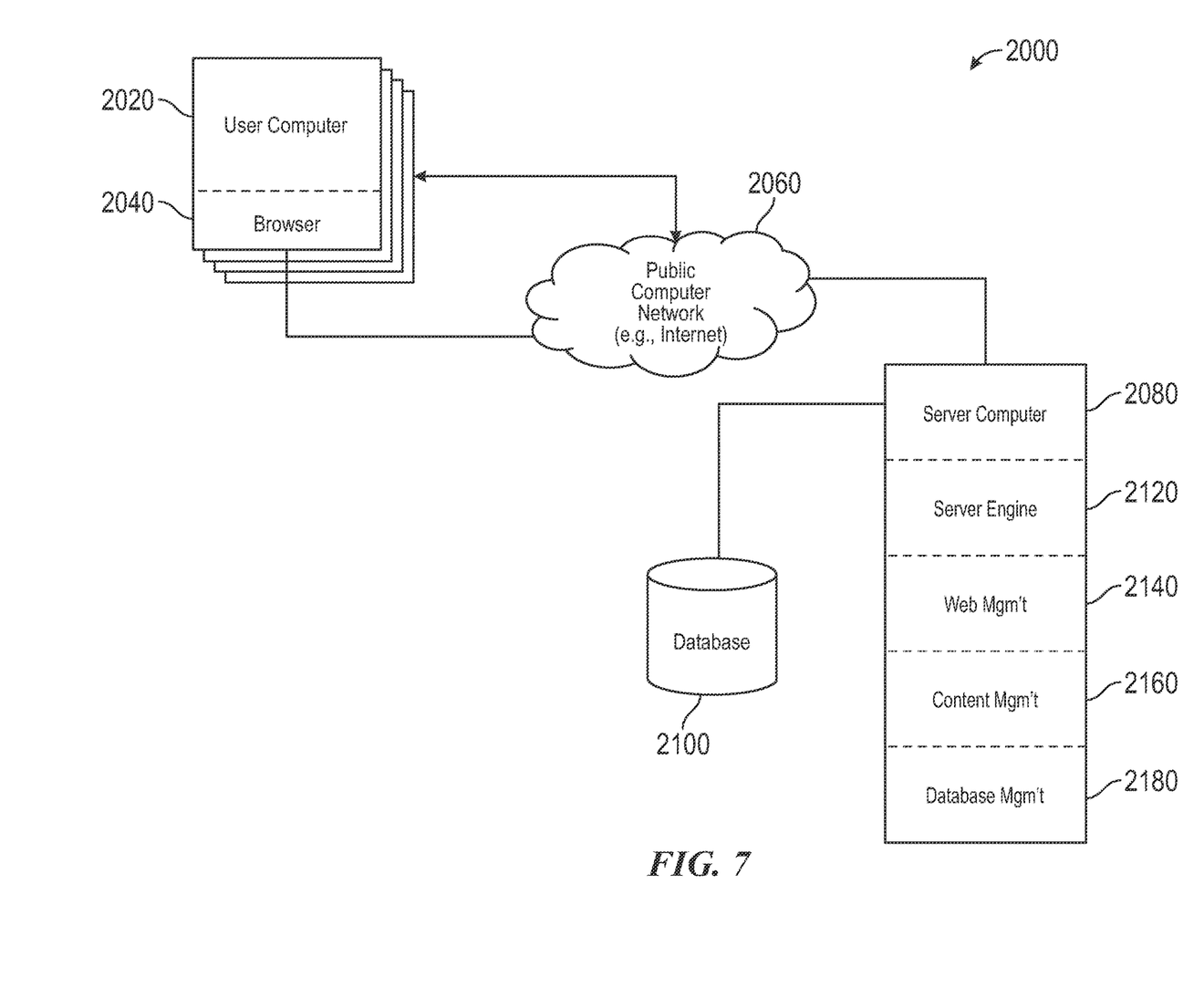
FIG. 7 is a block diagram illustrating a suitable system in which aspects of the various embodiments described herein may operate in a networked computer environment.

At least one server computer 2080, coupled to the Internet or World Wide Web ("Web") 2060, performs much or all of the functions for receiving, routing and storing of electronic messages, such as web pages, audio signals, and electronic images. While the Internet is shown, a private network, such as an intranet may indeed be preferred in some applications. The network may have a client-server architecture, in which a computer is dedicated to serving other client computers, or it may have other architectures such as a peer-to-peer, in which one or more computers serve simultaneously as servers and clients. A database 2100 or databases, coupled to the server computer(s), stores much of the web pages and content exchanged between the user computers. The server computer(s), including the database(s), may employ security measures to inhibit malicious attacks on the system, and to preserve integrity of the messages and data stored therein (e.g., firewall systems, secure socket layers (SSL), password protection schemes, encryption, and the like).

The server computer 2080 may include a server engine 2120, a web page management component 2140, a content management component 2160 and a database management component 2180. The server engine performs basic processing and operating system level tasks. The web page management component handles creation and display or routing of web pages. Users may access the server computer by means of a URL associated therewith. The content management component handles most of the functions in the embodiments described herein. The database management component includes storage and retrieval tasks with respect to the database, queries to the database, and storage of data.

FURTHER EXAMPLES

The following examples are illustrative of several embodiments of the present technology:

1. A mining detection system for mining shovels, the mining detection system comprising:
 a head assembly configured to be positioned at an inlet portion of a mining shovel bucket, the head assembly comprising—
  a camera unit comprising a multispectral imaging (MSI) camera unit and/or a hyperspectral imaging (HSI) camera unit, wherein the camera unit has a field of view and is configured to capture images of mining material prior to, during, and/or after loading the mining material into the mining shovel bucket;
  a lighting unit spaced apart from the camera unit and configured to illuminate an irradiation region, wherein at least a portion of the irradiation region overlaps with at least a portion of the field of view; and
  a sensor configured to detect characteristics of the mining material in the field of view; and
 a control component comprising a processing unit operably coupled to the head assembly.

2. The mining detection system of any one of the examples herein wherein the camera unit is a first camera unit, wherein the first camera unit is a compositional multispectral imaging (MSI) camera unit, and the head assembly further comprises a second camera unit, wherein the second camera unit is a compositional hyperspectral imaging (HSI) camera unit.

3. The mining detection system of any one of the examples herein wherein the camera unit comprises a lens and a band pass filter positioned over the lens, and wherein the head assembly further comprises a window configured to protect the camera unit.

4. The mining detection system of any one of the examples herein wherein the lighting unit is configured to emit light having a predefined wavelength range corresponding to a camera wavelength range detectable by the camera unit.

5. The mining detection system of any one of the examples herein wherein the lighting unit is configured to emit light having a predefined wavelength range different from a camera wavelength range detectable by the camera unit.

6. The mining detection system of any one of the examples herein wherein the camera unit and the lighting unit are downward looking such that the field of view and the irradiation region are configured to be directed into the mining shovel bucket.

7. The mining detection system of any one of the examples herein wherein the processing unit is configured to determine a material composition of the mining material based on the images captured by the imaging system.

8. The mining detection system of any one of the examples herein wherein the sensor is an in-cheek sensor configured to be positioned on a side wall portion of the mining shovel bucket.

9. The mining detection system of any one of the examples herein wherein the sensor is positioned between the camera unit and the lighting unit.

10. The mining detection system of any one of the examples herein wherein the sensor is a proximity sensor configured to determine whether the mining material is within a depth of field (DOF) of the camera unit, and wherein the mining detection system further comprises a shutter positioned to protect a lens of the camera unit, the shutter being operably coupled to the proximity sensor such that the proximity sensor is configured to actuate the shutter when the mining material is within the DOF.

11. The mining detection system of any one of the examples herein wherein the sensor is a radiometric sensor, a photometric sensor, and/or an electromagnetic sensor.

12. The mining detection system of any one of the examples herein wherein the control component is configured to, based on the images from the camera unit, classify the mining material in one of the following categories: high oxide, low oxide, or oxide-absent.

13. The mining detection system of any one of the examples herein wherein the sensor is an x-ray fluorescence sensor configured to determine a percent of copper in the mining material.

14. The mining detection system of any one of the examples herein wherein the head assembly is housed within a ruggedized and/or non-metallic material configured to not interfere with operation of the sensor.

15. A mining detection system for mining shovels, the mining detection system comprising:
- a head assembly configured to be positioned at an inlet portion of a mining shovel bucket, the head assembly comprising—
  - a camera unit comprising a multispectral imaging (MSI) camera unit and/or a hyperspectral imaging (HSI) camera unit, wherein the camera unit has a field of view and is configured to capture images of mining material prior to, during, and/or after loading the mining material into the mining shovel bucket; and
  - a lighting unit spaced apart from the camera unit and configured to illuminate an irradiation region, wherein at least a portion of the irradiation region overlaps with at least a portion of the field of view; and
- a control component comprising a processing unit operably coupled to the head assembly.

16. The mining detection system of any one of the examples herein, further comprising a mining shovel bucket, wherein the head assembly is positioned at an inlet portion, an upper wall portion of, at an interior side wall portion of, or above the mining shovel bucket.

17. The mining detection system of example 16 wherein the control component is positioned at an exterior upper wall portion of the mining shovel bucket.

18. The mining detection system of any one of the examples herein further comprising a sensor configured to detect characteristics of the mining material in the field of view.

19. The mining detection system of example 18 wherein the sensor is an in-cheek sensor positioned on a first side wall portion, a second side wall portion, or an upper wall portion of the mining shovel bucket.

20. The mining detection system of example 18 wherein the sensor is a peripheral sensor positioned on an inlet portion of the mining shovel bucket and between the camera unit and the lighting unit.

21. A method of classifying and sorting mining material at a mine site, the method comprising:
- receiving the mining material in an interior region of a mining shovel bucket;
- capturing images of the mining material entering or within the interior region using a camera unit positioned at an inlet portion of the mining shovel bucket, wherein the camera unit comprises a compositional multispectral imaging (MSI) camera unit and/or a compositional hyperspectral imaging (HSI) camera unit; and
- processing, via a control component operably coupled to the camera unit, the images captured by the camera unit to identify compositional properties of the mining material.

22. The method of any one of the examples herein, further comprising illuminating at least a portion of a field of view of the camera unit while the camera unit is capturing images of the mining material.

23. The method of any one of the examples herein, further comprising:
- determining, via a proximity sensor, whether the mining material is within a depth of field (DOF) of the camera unit; and
- initiating the capture of images via the camera unit when in the DOF.

24. The method of any one of the examples herein, further comprising determining, via an x-ray fluorescence sensor, a percent of copper in the mining material.

25. The method of any one of the examples herein wherein the images are captured by the camera unit with a flash.

26. The method of any one of the examples herein wherein the images are captured by the camera unit without a flash.

27. The method of any one of the examples herein further comprising classifying the mining material, based on the images captured by the camera unit, in one of the following categories: high oxide, low oxide, or oxide-absent.

28. The method of example 27 further comprising sorting the mining material based on the categories.

CONCLUSION

In general, the detailed description of embodiments of the present technology is not intended to be exhaustive or to limit the invention to the precise form disclosed above. While specific embodiments of, and examples for, the present technology are described above for illustrative purposes, various equivalent modifications are possible within the scope of the present technology, as those skilled in the relevant art will recognize. For example, while processes or blocks are presented in a given order, alternative embodiments may perform routines having steps, or employ systems having blocks, in a different order, and some processes or blocks may be deleted, moved, added, subdivided, combined, and/or modified. Each of these processes or blocks may be implemented in a variety of different ways. Also, while processes or blocks are at times shown as being performed in series, these processes or blocks may instead be performed in parallel, or may be performed at different times.

Aspects of the present technology may be stored or distributed on computer-readable media, including magnetically or optically readable computer discs, hard-wired or preprogrammed chips (e.g., EEPROM semiconductor chips), nanotechnology memory, biological memory, or other data storage media. Alternatively, computer implemented instructions, data structures, screen displays, and other data under aspects of the present technology may be distributed over the Internet or over other networks (including wireless networks), on a propagated signal on a propagation medium (e.g., an electromagnetic wave(s), a sound wave, etc.) over a period of time, or they may be provided on any analog or digital network (packet switched, circuit switched, or other scheme). Those skilled in the relevant art will recognize that portions of the present technology reside on a server computer, while corresponding portions reside on a client computer such as a mobile or portable device, and thus, while certain hardware platforms are described herein, aspects of the present technology are equally applicable to nodes on a network.

The teachings of the present technology provided herein can be applied to other systems, not necessarily the system described herein. The elements and acts of the various embodiments described herein can be combined to provide further embodiments.

Any patents, applications and other references, including any that may be listed in accompanying filing papers, are incorporated herein by reference. Aspects of the present technology can be modified, if necessary, to employ the systems, functions, and concepts of the various references described above to provide yet further embodiments of the present technology.

These and other changes can be made to the present technology in light of the above Detailed Description. While the above description details certain embodiments of the present technology and describes the best mode contemplated, no matter how detailed the above appears in text, the present technology can be practiced in many ways. Details of the present technology may vary considerably in its implementation details, while still being encompassed by the present technology disclosed herein. As noted above, particular terminology used when describing certain features or aspects of the present technology should not be taken to imply that the terminology is being redefined herein to be restricted to any specific characteristics, features, or aspects of the present technology with which that terminology is associated. In general, the terms used in the following claims should not be construed to limit the present technology to the specific embodiments disclosed in the specification, unless the above Detailed Description section explicitly defines such terms. Accordingly, the actual scope of the invention encompasses not only the disclosed embodiments, but also all equivalent ways of practicing or implementing the present technology.

We claim:

1. A mining detection system for mining shovels, the mining detection system comprising:
    a head assembly configured to be positioned at an inlet portion of a mining shovel bucket, the head assembly comprising:
        a camera unit comprising a multispectral imaging (MSI) camera unit and/or a hyperspectral imaging (HSI) camera unit, wherein the camera unit has a field of view and is configured to capture images of mining material prior to, during, and/or after loading the mining material into the mining shovel bucket;
        a lighting unit spaced apart from the camera unit and configured to illuminate an irradiation region, wherein at least a portion of the irradiation region overlaps with at least a portion of the field of view;
        a sensor configured to detect characteristics of the mining material in the field of view; the sensor is a proximity sensor configured to determine whether the mining material is within a depth of field (DOF) of the camera unit, and wherein the mining detection system further comprises a shutter positioned to protect a lens of the camera unit, the shutter being operably coupled to the proximity sensor such that the proximity sensor is configured to actuate the shutter when the mining material is within the DOF; and
    a control component comprising a processing unit operably coupled to the head assembly.

2. The mining detection system of claim 1 wherein the camera unit is a first camera unit, wherein the first camera unit is a compositional multispectral imaging (MSI) camera unit, and the head assembly further comprises a second camera unit, wherein the second camera unit is a compositional hyperspectral imaging (HSI) camera unit.

3. The mining detection system of claim 1 wherein the camera unit comprises a lens and a band pass filter positioned over the lens.

4. The mining detection system of claim 1 wherein the lighting unit is configured to emit light having a predefined wavelength range corresponding to a camera wavelength range detectable by the camera unit.

5. The mining detection system of claim 1 wherein the lighting unit is configured to emit light having a predefined wavelength range different from a camera wavelength range detectable by the camera unit.

6. The mining detection system of claim 1 wherein the camera unit and the lighting unit are downward looking such that the field of view and the irradiation region are configured to be directed into the mining shovel bucket.

7. The mining detection system of claim 1 wherein the processing unit is configured to determine a material composition of the mining material based on the images captured by the imaging system.

8. The mining detection system of claim 1 wherein the sensor is positioned between the camera unit and the lighting unit.

9. The mining detection system of claim 1 wherein the head assembly is housed within a ruggedized and/or non-metallic material configured to not interfere with operation of the sensor.

10. The mining detection system of claim 1, further comprising a mining shovel bucket, wherein the head assembly is positioned at an inlet portion, an upper wall portion of, at an interior side wall portion of, or above the mining shovel bucket.

11. The mining detection system of claim 10 wherein the control component is positioned at an exterior upper wall portion of the mining shovel bucket.

12. A mining detection system for mining shovels, the mining detection system comprising:
    a head assembly configured to be positioned at an inlet portion of a mining shovel bucket, the head assembly comprising:
        a camera unit comprising a multispectral imaging (MSI) camera unit and/or a hyperspectral imaging (HSI) camera unit, wherein the camera unit has a field of view and is configured to capture images of mining material prior to, during, and/or after loading the mining material into the mining shovel bucket;
        a lighting unit spaced apart from the camera unit and configured to illuminate an irradiation region, wherein at least a portion of the irradiation region overlaps with at least a portion of the field of view;
        a sensor configured to detect characteristics of the mining material in the field of view; and
    a control component comprising a processing unit operably coupled to the head assembly, the control component is configured to, based on the images from the camera unit, classify the mining material in one of the following categories: high oxide, low oxide, or oxide-absent.

13. The mining detection system of claim 12, further comprising a mining shovel bucket, wherein the head assembly is positioned at an inlet portion, an upper wall portion of, at an interior side wall portion of, or above the mining shovel bucket.

14. The mining detection system of claim 13, wherein the control component is positioned at an exterior upper wall portion of the mining shovel bucket.

15. A mining detection system for mining shovels, the mining detection system comprising:
    a head assembly configured to be positioned at an inlet portion of a mining shovel bucket, the head assembly comprising:
        a camera unit comprising a multispectral imaging (MSI) camera unit and/or a hyperspectral imaging (HSI) camera unit, wherein the camera unit has a field of view and is configured to capture images of mining material prior to, during, and/or after loading the mining material into the mining shovel bucket;

a lighting unit spaced apart from the camera unit and configured to illuminate an irradiation region, wherein at least a portion of the irradiation region overlaps with at least a portion of the field of view;

a sensor configured to detect characteristics of the mining material in the field of view, wherein the sensor is an x-ray fluorescence sensor configured to determine a percent of copper in the mining material; and a control component comprising a processing unit operably coupled to the head assembly.

16. The mining detection system of claim 15, further comprising a mining shovel bucket, wherein the head assembly is positioned at an inlet portion, an upper wall portion of, at an interior side wall portion of, or above the mining shovel bucket.

17. The mining detection system of claim 16, wherein the control component is positioned at an exterior upper wall portion of the mining shovel bucket.

18. A method of classifying and sorting mining material at a mine site, the method comprising:

receiving the mining material in an interior region of a mining shovel bucket;

capturing images of the mining material entering or within the interior region using a camera unit positioned at an inlet portion of the mining shovel bucket, wherein the camera unit comprises a compositional multispectral imaging (MSI) camera unit and/or a compositional hyperspectral imaging (HSI) camera unit;

processing, via a control component operably coupled to the camera unit, the images captured by the camera unit to identify compositional properties of the mining material;

determining, via a proximity sensor, whether the mining material is within a depth of field (DOF) of the camera unit; and initiating the capture of the images via the camera unit when in the DOF.

19. The method of claim 18, further comprising illuminating at least a portion of a field of view of the camera unit while the camera unit is capturing images of the mining material.

20. The method of claim 18 wherein the images are captured by the camera unit with a flash.

21. The method of claim 18 wherein the images are captured by the camera unit without a flash.

22. A method of classifying and sorting mining material at a mine site, the method comprising:

receiving the mining material in an interior region of a mining shovel bucket;

capturing images of the mining material entering or within the interior region using a camera unit positioned at an inlet portion of the mining shovel bucket, wherein the camera unit comprises a compositional multispectral imaging (MSI) camera unit and/or a compositional hyperspectral imaging (HSI) camera unit; and processing, via a control component operably coupled to the camera unit, the images captured by the camera unit to identify compositional properties of the mining material; and determining, via an x-ray fluorescence sensor, a percent of copper in the mining material.

23. The method of claim 22, further comprising illuminating at least a portion of a field of view of the camera unit while the camera unit is capturing images of the mining material.

24. The method of claim 22, wherein the images are captured by the camera unit with a flash.

25. The method of claim 22, wherein the images are captured by the camera unit without a flash.

26. A method of classifying and sorting mining material at a mine site, the method comprising:

receiving the mining material in an interior region of a mining shovel bucket;

capturing images of the mining material entering or within the interior region using a camera unit positioned at an inlet portion of the mining shovel bucket, wherein the camera unit comprises a compositional multispectral imaging (MSI) camera unit and/or a compositional hyperspectral imaging (HSI) camera unit; and processing, via a control component operably coupled to the camera unit, the images captured by the camera unit to identify compositional properties of the mining material; and classifying the mining material, based on the images captured by the camera unit, in one of the following categories: high oxide, low oxide, or oxide-absent.

27. A method of classifying and sorting mining material at a mine site, the method comprising:

receiving the mining material in an interior region of a mining shovel bucket;

capturing images of the mining material entering or within the interior region using a camera unit positioned at an inlet portion of the mining shovel bucket, wherein the camera unit comprises a compositional multispectral imaging (MSI) camera unit and/or a compositional hyperspectral imaging (HSI) camera unit; and processing, via a control component operably coupled to the camera unit, the images captured by the camera unit to identify compositional properties of the mining material; and sorting the mining material based on the categories.

* * * * *